(12) United States Patent
Sanghera et al.

(10) Patent No.: US 8,588,895 B2
(45) Date of Patent: Nov. 19, 2013

(54) ROBUST RATE CALCULATION IN AN IMPLANTABLE CARDIAC STIMULUS OR MONITORING DEVICE

(75) Inventors: Rick Sanghera, San Clemente, CA (US); Venugopal Allavatam, San Clemente, CA (US); Jay A. Warren, San Juan Capistrano, CA (US); Mark R. Schroeder, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 0 days.

(21) Appl. No.: 13/451,393

(22) Filed: Apr. 19, 2012

(65) Prior Publication Data

US 2012/0271185 A1    Oct. 25, 2012

Related U.S. Application Data

(60) Provisional application No. 61/478,277, filed on Apr. 22, 2011.

(51) Int. Cl.
*A61B 5/04*    (2006.01)
(52) U.S. Cl.
USPC .......................................................... 600/516
(58) Field of Classification Search
USPC .......................................... 600/516, 515, 518
See application file for complete search history.

(56) References Cited

U.S. PATENT DOCUMENTS

| | | | |
|---|---|---|---|
| 5,817,027 A * | 10/1998 | Arand et al. .................. | 600/515 |
| 5,941,831 A | 8/1999 | Turcott | |
| 2002/0147474 A1 | 10/2002 | Seim et al. | |
| 2006/0178704 A1 | 8/2006 | Elahi et al. | |
| 2006/0217621 A1 | 9/2006 | Kim et al. | |
| 2006/0287605 A1 | 12/2006 | Lin et al. | |
| 2009/0187227 A1 | 7/2009 | Palreddy et al. | |
| 2009/0264783 A1* | 10/2009 | Xi et al. ........................ | 600/518 |

FOREIGN PATENT DOCUMENTS

| WO | WO-9848891 A1 | 11/1998 |
|---|---|---|
| WO | WO-2009111766 A2 | 9/2009 |
| WO | WO-2012145600 A2 | 10/2012 |

OTHER PUBLICATIONS

"International Application Serial No. PCT/US2012/034412, Search Report mailed Dec. 19, 2012", 6 pgs.
"International Application Serial No. PCT/US2012/034412, Written Opinion mailed Dec. 19, 2012", 15 pgs.

* cited by examiner

*Primary Examiner* — Robert N Wieland
(74) *Attorney, Agent, or Firm* — Schwegman Lundberg & Woessner, P.A.

(57) ABSTRACT

Devices and methods for analyzing cardiac signal data. An illustrative method includes identifying a plurality of detected events and measuring intervals between the detected events for use in rate estimation. In the illustrative embodiment, a set of intervals is used to make the rate estimation by first discarding selected intervals from the set. The remaining intervals are then used to calculate an estimated interval, for example by averaging the remaining intervals.

20 Claims, 15 Drawing Sheets

| Detection | Int. Type | Duration | 4 Int. Rate | Classify | 5/8 Rate | Classify |
|---|---|---|---|---|---|---|
| R | R-R | 420 | 190 | VT | 172 | OK |
| R | R-R | 420 | 190 | VT | 172 | OK |
| R | R-T | 180 | 235 | VF | 200 | VT |
| T | T-R | 240 | 222 | VT | 192 | VT |
| R | R-R | 420 | 190 | VT | 200 | VT |
| R | R-T | 180 | 190 | VT | 227 | VT |
| T | T-R | 240 | 190 | VT | 192 | VT |
| R | R-R | 420 | 190 | VT | 172 | OK |
| R | R-R | 420 | 235 | VF | 172 | OK |
| R | R-T | 180 | 286 | VF | 172 | OK |
| T | T-R | 240 | 222 | VT | 156 | OK |
| R | R-T | 180 | 190 | VT | 143 | OK |
| T | T-R | 240 | 160 | OK | 143 | OK |
| R | R-R | 420 | 143 | OK | 143 | OK |
| R | R-R | 420 | 143 | OK | 143 | OK |
| R | R-R | 420 | 143 | OK | 143 | OK |
| R | R-R | 420 | 167 | OK | 156 | OK |
| R | R-R | 420 | 190 | VT | 172 | OK |
| R | R-R | 420 | 190 | VT | 172 | OK |
| R | R-T | 180 | 190 | VT | 179 | OK |
| T | T-R | 240 | 190 | VT | 192 | VT |
| R | R-R | 420 | 190 | VT | 172 | OK |
| R | R-R | 420 | 190 | VT | 172 | OK |
| R | R-T | 180 | 235 | VF | | |
| T | T-R | 240 | 222 | VT | | |
| R | R-R | 420 | 190 | VT | | |
| R | R-T | 180 | 190 | VT | | |
| T | T-R | 240 | | | | |
| R | R-R | 420 | | | | |
| R | R-R | 420 | | | | |
| R | | | | | | |

196

| Four Intervals | | 5/8 Intervals | |
|---|---|---|---|
| OK | 5 | OK | 17 |
| VT | 18 | VT | 6 |
| VF | 4 | VF | 0 | ary
ROBUST RATE CALCULATION IN AN IMPLANTABLE CARDIAC STIMULUS OR MONITORING DEVICE

RELATED APPLICATIONS

The present application claims the benefits of and priority to U.S. Provisional Patent Application No. 61/478,277, filed Apr. 22, 2011, titled ROBUST RATE CALCULATION IN AN IMPLANTABLE CARDIAC STIMULUS OR MONITORING DEVICE, the disclosure of which is incorporated herein by reference.

FIELD

The present invention relates to the field of implantable medical devices. More particularly, the present invention relates to devices and methods of operation for implantable cardiac stimulus or monitoring.

BACKGROUND

Implantable cardiac devices typically sense cardiac electrical signals in an implantee and classify the implantee's cardiac rhythm as normal/benign or malignant. Illustrative malignant tachyarrhythmias include ventricular fibrillation and polymorphic ventricular tachyarrhythmia. Other tachycardia or bradycardia conditions may be of interest as well. The accuracy with which an implantable medical device analyzes sensed signals determines how well it makes therapy determinations and other decisions. Incorrect rate calculation can lead to inappropriate classification of cardiac activity. For example, calculation of an erroneously high cardiac rate can cause a system to identify a cardiac arrhythmia that may not actually be occurring. Inappropriate classification can, in turn, lead to incorrect therapy decisions.

SUMMARY

The present invention, in an illustrative embodiment, comprises a method for analyzing cardiac signal data. The illustrative method includes identifying a plurality of detected events and measuring intervals between the detected events, which are then used incardiac rate estimation. In the illustrative embodiment, a set of intervals is used to make the rate estimation by first discarding selected intervals from the set. The remaining intervals are then used to calculate an estimated rate. Devices for performing such methods are also disclosed. Additional embodiments and other solutions are explained as well.

DETAILED DESCRIPTION

The following detailed description should be read with reference to the drawings. The drawings, which are not necessarily to scale, depict illustrative embodiments and are not intended to limit the scope of the invention. Unless implicitly required or explicitly stated, the illustrations of methods herein should not be read to require any particular order of steps.

As used herein, a signal is sensed by an implantable cardiac device system, events are detected in the sensed signal, and cardiac rhythms are classified by use of the detected events. Detected events may also be referred to as detections. Cardiac rhythm classification can include identification of malignant conditions, such as ventricular fibrillation or certain tachyarrhythmias, for example. Implantable therapy systems make therapy/stimulus decisions in reliance upon the classification of the cardiac rhythm, while monitoring systems make data recording decision using rhythm classification, where applicable, and all such systems can, if so configured, generate annunciating (audible tones or palpable vibrations) or communicating (telemetry) signals in response to rhythm classification.

When detecting events, an implantable cardiac device may compare the sensed signal to a detection threshold. If/when the sensed signal crosses the detection threshold, a new detected event is declared. The detection threshold may be static or may change with time (or by dependence on other variables such as observed signal frequency), depending upon the system configuration. In some systems the detection threshold has a shape defined by a detection profile which can be applied anew after each detected event.

A cardiac cycle typically includes several portions (often referenced as "waves") which, according to well known convention, are labeled with letters including P, Q, R, S, and T, each corresponding to certain physiological events. Each cardiac cycle usually has all of these parts, though not all may be visible on any given cardiac signal representation. Certain components may not be visible due to factors such as elevated rate, choice of sensing vector, anatomic anomaly, or active arrhythmia, for example.

Figure 1:
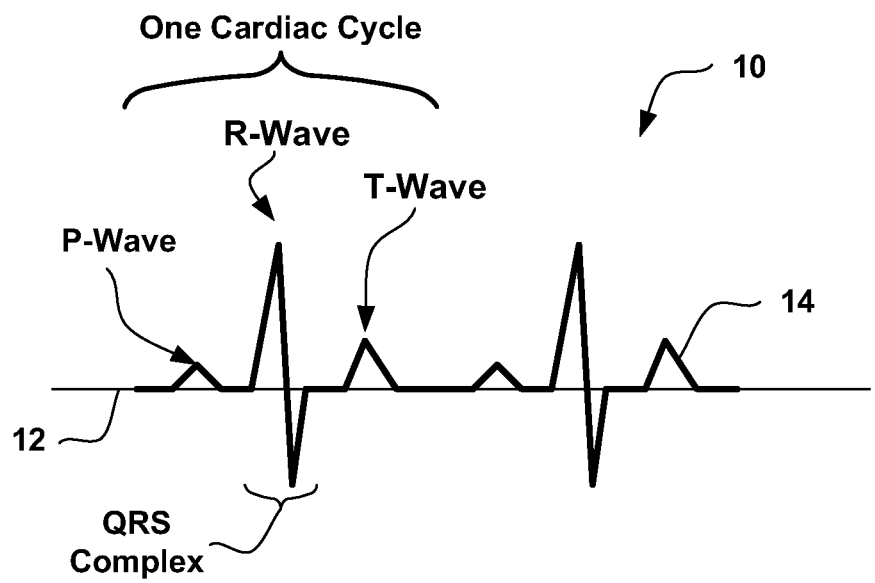
FIG. 1 illustrates a cardiac signal.

FIG. 1 illustrates a cardiac electrical signal, shown at 10 along baseline 12, with the R-wave and QRS complex indicated. The T-wave follows the QRS complex, and the P-wave precedes the QRS complex. It is typical to design cardiac signal analysis methods to include detection of the R-wave or QRS complex in order to estimate the rate at which cardiac cycles occur. However, any repeatably detectable segment or portion of the cardiac cycle may be used for detection.

Figure 2:
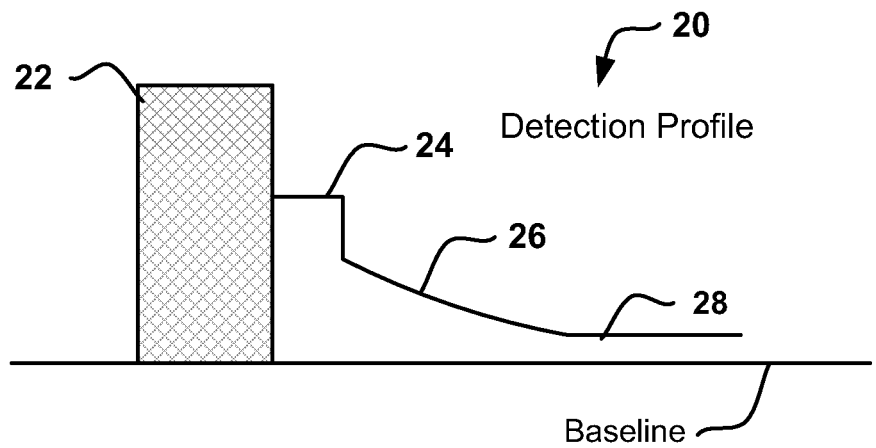
FIGS. 2-3 show an illustrative detection profile useful for identifying cardiac cycles and detections and intervals generated when using the detection profile to identify cardiac cycles.

One method for detecting cardiac events (heart "beats") is to apply a detection profile, an example of which is shown in FIG. 2. The detection profile 20 is shown relative to a Baseline and includes a refractory period 22 followed by a detection threshold having several segments at 24, 26 and 28. In one example, during the refractory period 22, the system does not recognize additional detections, regardless of the signal shape or amplitude. The detection profile 20 may, in one example, be iteratively compared to the sensed signal by aligning the start (the leftmost point) of the refractory period 22 with the detection of a previously detected event and setting the height of the detection profile relative to an estimate of the peak amplitude of the cardiac signal. When the sensed signal crosses outside of the refractory period 22, a new detected event is declared and a new iteration of detection starts by aligning the start of the refractory period 22 with the most recent detection and adjusting the peak estimate. US. Patent Application Publication No. 20090228057, titled ACCURATE CARDIAC EVENT DETECTION IN AN IMPLANTABLE CARDIAC STIMULUS DEVICE, the disclosure of which is incorporated herein by reference, discusses some illustrative features for and methods of using detection profiles.

The aim with the detection profile 20 shown in FIG. 2 is to predictably detect cardiac events as shown at 10 in FIG. 1. For many systems, the goal is one-to-one detection in which one detected event is declared for each cardiac cycle. Overdetection may occur if a device or method declares more than one detected event within a single cardiac cycle. Examples include the detection of both an R-wave and a trailing T-wave as well as multiple detections of an R-wave or QRS complex. Some systems, for example dual chamber systems, may intentionally detect two parts of the cardiac cycle using separate sensing channels (such as an atrial sense and a ventricular sense); for such a system, overcounting can manifest as more than the intended quantity (and/or type) of detection occurring in a cardiac cycle.

Those skilled in the art understand that detection accuracy in cardiac devices can be challenged by any number of variations of "normal" cardiac activity. For example, a P-wave may be detected and followed by detection of a trailing part of the QRS or a T-wave from the same cardiac cycle in a single sensing channel. Overdetection may also occur if one of various potential noise sources causes an event to be declared, for example, due to external therapy or noise, pacing or motion artifact, and/or non-cardiac muscle noise, etc.

Figure 3:
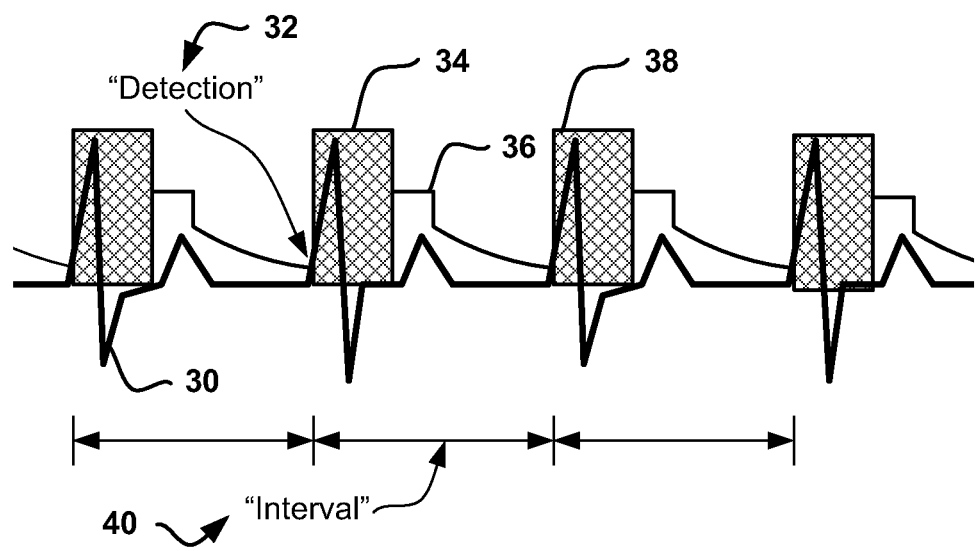
Figure 4:
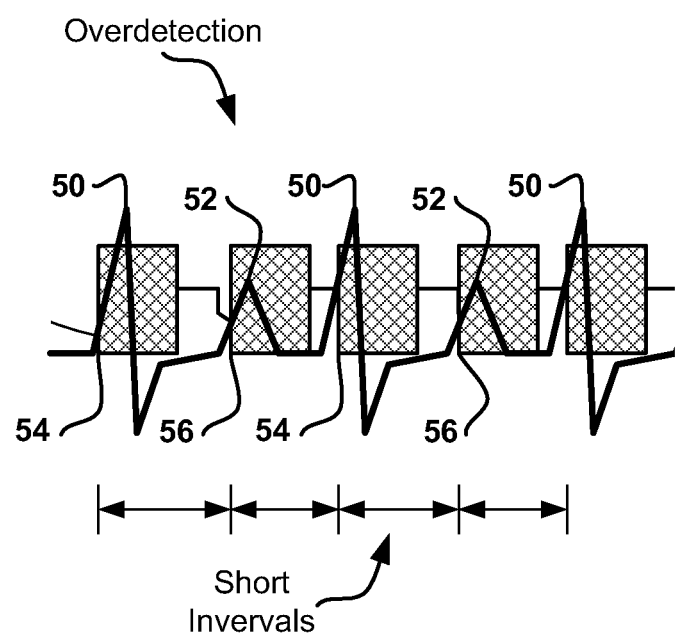
FIG. 4 illustrates analysis when a detection profile of FIG. 2 overdetects cardiac cycles.

FIG. 3 shows accurate, one-to-one detection in which one detected event is declared for each cardiac cycle. The cardiac signal is shown at 30. The cardiac signal is compared to a detection threshold that is itself defined by the detection profile (FIG. 2). As noted at 32, a detection is declared when the cardiac signal 30 crosses the detection threshold. This triggers the detection threshold to enter refractory 34 and then follow the shape defined by the detection profile after refractory 34, as shown at 36. One intended purpose of refractory 34 is to inhibit multiple detections due to a single R-wave or QRS complex. When the detection threshold is crossed again, another new detected event is declared, as shown at 38. The period between consecutive detections is defined as the interval 40. The intervals 40 between the detections can be used to estimate or calculate the cardiac rate. As a contrast to FIG. 3, FIG. 4 shows consistent overdetection. Here, the cardiac signal is shown as having R-waves at 50 and T-waves at 52. In the example, cardiac cycles are overdetected, yielding twice as many detected events as R-waves. Thus there are detections 54 and 56 for consecutive R and T waves 50, 52. If one cardiac cycle takes place but a device declares multiple detected events, overdetection has occurred. If beat rate is calculated by using multiple detections of a single cardiac cycle, overcounting occurs. Overdetection can lead to overcounted cardiac cycles, shortened intervals and inflated rate estimates.

It is worth noting that overdetection has many potential root causes. The purpose of implantable cardiac devices is to monitor and (for those so equipped) treat abnormal cardiac behavior. Abnormal cardiac behavior includes numerous broad categories, such as atrial fibrillation, ventricular tachycardia, and ventricular fibrillation, as well as subcategories and subclasses. Abnormal cardiac behavior may be inherent in physiology, may result from disease condition or progression, may occur due to injury and recovery, may stem from drug use or misuse, or may have other or unknown causes. Overdetection is, in some instances, a deficiency in the implementation of an algorithm for cardiac event detection. In other instances, overdetection is a result of a very complex electrogram, or an electrogram of insufficient amplitude for the detection system. Designing one system to handle all such inputs can include provisions for avoiding inappropriate therapy in response to overdetection that eludes tailored detection and/or confounds efforts to handle overdetection. The present invention, in an illustrative embodiment, adopts provisions for avoiding inappropriate therapy in the manner in which cardiac rates are calculated using cardiac event detection.

Figure 5:
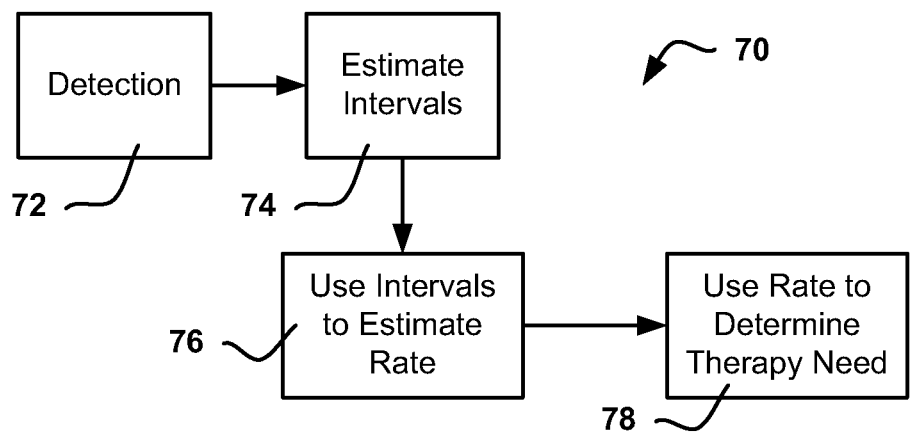
FIG. 5 shows, in block form, a method of analysis in an implantable cardiac stimulus device.

FIG. 5 shows an illustrative therapy decision method. The method, shown at 70, includes detection 72 which yields intervals 74. The intervals 74 can be used to estimate rate 76, and rate 76 can be used to determine therapy need 78. Some implantable systems, such as implantable defibrillators, are designed to identify tachyarrhythmias (dangerous high-rate conditions). If overdetection leads to overcounting, yielding incorrectly short intervals and high rate calculations, the risk of inappropriate therapy due to overdetection is increased.

When overdetection occurs, some solutions include identifying the overdetection condition and reducing the calculated rate and/or suspending rhythm classification. Another solution is to identify individual overdetections and correct related data, omitting the overdetections and recalculating intervals and/or rate, as shown, for example, in US Patent Application Publication Numbers 20090259271 (now U.S. Pat. No. 8,160,686) and 20100004713 (now U.S. Pat. No. 8,160,687), each titled METHODS AND DEVICES FOR ACCURATELY CLASSIFYING CARDIAC ACTIVITY, US Patent Application Publication 20110098585 (now U.S. Pat. No. 8,265,737), titled METHODS AND DEVICES FOR IDENTIFYING OVERDETECTION OF CARDIAC SIGNALS, and U.S. patent application Ser. No. 13/214,099 (now US Pub. Pat. App. 20120046563), titled METHODS AND DEVICES THAT IDENTIFY OVERDETECTION IN IMPLANTABLE CARDIAC SYSTEMS, which claims the benefit of U.S. Provisional Patent Application 61/375,732, the disclosures of which are each incorporated herein by reference. Additional and/or alternative approaches are desirable.

Figure 6:
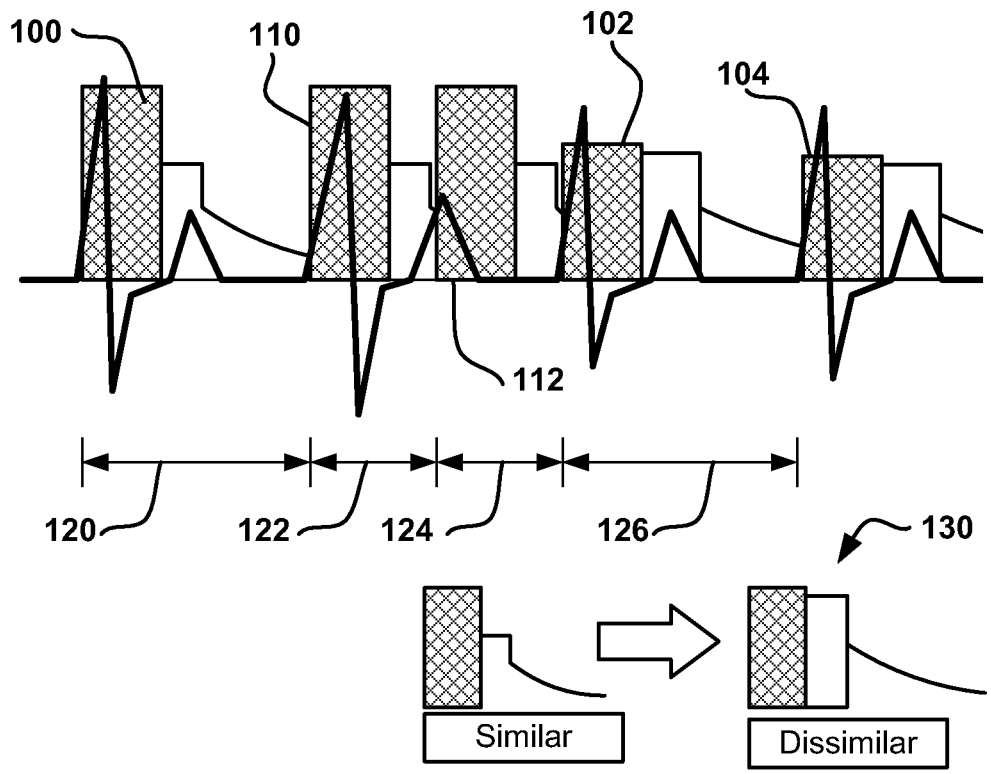
FIG. 6 illustrates a single overdetection among several detections of cardiac cycles.

FIG. 6 shows an example of relatively sporadic overdetection. Several R-waves and cardiac cycles are accurately detected, including at 100, 102 and 104. However, the cardiac cycle at 110 is counted twice, as the T-wave crosses the detection threshold and creates an extra detection at 112. Thus the longer intervals at 120 and 126 are separated by two short intervals at 122 and 124. Overdetection in this instance is caused by two factors: first, the T-wave is large relative to the R-wave, with the R:T ratio, in amplitude, at about 2:1. Second, the peak amplitudes are varying over time, meaning that from cycle to cycle the sensed signal varies between larger and smaller amplitudes. If the ratio of R:T becomes smaller, overdetection may be more consistent, and pattern identification may identify the overdetection. As the R:T ratio approaches 1:1, overdetection can become prevalent and corrective action may be needed, such as reprogramming the sense vector.

In the example shown, overdetections are avoided at 102 and 104 due to a modification to the detection profile. As highlighted at 130, the detection profile changes from a first profile used when amplitude peaks of consecutive detected events are similar to a second profile used when amplitude peaks of consecutive detected events are dissimilar. This concept is further explained in US Patent Application Publication Number 20090228057, which is incorporated herein by reference. More particularly, because the amplitudes of detected events 110, 112 vary greatly from one to the next, a different detection profile is applied at 102 and 104 than was applied to detections 100, 110 and 112. This modification can avoid some overdetections, but does not necessarily correct overcounting of event 112. As explained in US Patent Application Publication Number 20090228057, the result can be repetitive sets of two accurately detected cardiac cycles followed by one double-detected cardiac cycle.

If sporadic overdetection/overcounting occurs at a relatively low cardiac rate, the risk of inappropriate shock can remain low. For example, if a system uses an average of four intervals to calculate rate, one extra detection at 75 beats-per-minute (bpm) would increase the calculated rate to 85 bpm for one calculation, 100 bpm (600 millisecond cycle length) for three calculations, and once more to about 85 bpm for an additional calculation. Many implantable systems are designed or may be configured to leave a 100 bpm rate untreated. For such systems, little to no risk of inappropriate therapy is created by sporadic overdetection or overcounting in a low rate range.

However, if the occasional overdetection occurs while the cardiac rate is higher due to a nonpathological condition (i.e. exercise induced tachycardia), incorrect tachyarrhythmia detection may occur. For example, again using a four interval average, one overdetection on a 150 bpm (400 ms average interval) intrinsic rhythm would cause rate calculations to increase to about 170 bpm for one calculation, then to 200 bpm for three calculations, and back to 170 bpm for one calculation. Many implantable systems are designed or can be configured to classify rates at 170 bpm and/or 200 bpm or more as tachyarrhythmic. Further, such systems are often configured to treat tachyarrhythmias in this range, based on the assumption that the rate indicates a pathologic condition. A likelihood of inappropriate therapy can be created by overdetection and overcounting that results in incorrectly elevated rate calculation in this range.

The impact of overcounting can be compounded by the use of interval averaging. For example, systems can use, for example, up eight intervals (more, in some instances) to generate a rate estimation by averaging or weighting the intervals to create a typical interval estimate. For purposes of examples herein, four equally weighted intervals are used as a point of reference, though other numbers of intervals and weights may be used instead. Using a four interval average, if one in three cardiac cycles is overdetected, over the course of twelve cardiac cycles, a set of resulting detections may appear as follows:

{R, R, R, R, T, R, R, R, R, T, R, R, R, R, T, R R, R, T, R, R, R, R, R}

Where R represents R-wave detection and T is an overdetected T wave (Three preceding and five following R-wave detections are represented to allow fuller analysis). The intervals would then be:

{L, L, L, S, S, L, L, L, S, S, L, L, L, S, S, L, L, S, S, L, L, L, L}

Where L indicates a longer interval between two R-waves, and S is a shortened interval taking the form of either R-T or T-R. Because a detected event must appear at the start and end of the series of intervals, there is one less interval than the number of detected events in the illustration. If the R-waves are regularly spaced in time, two consecutive "S" intervals equal one L interval. If four R-R intervals are used to calculate rate, rate calculations would be:

{E, F, F, F, E, E, F, F, F, E, E, F, F, F, F, F, F, E, N}

Where N is a normal rate calculation with no shortened intervals, F is a fast rate calculation with two shortened intervals, and E is an elevated rate calculation that is above the actual rate due to having one shortened interval. For the sequence shown, only one of the rate calculations is correct, and the other nineteen are inflated above the actual rate. Thirteen of the twenty rate calculations are fast (F), and another six rate calculations are elevated above the actual rate (E). This occurs even though most the cardiac cycles were correctly detected, and even in the presence of several correct detections before and after the overdetections occur. An alternative to this method of rate calculation is sought.

Figure 7:
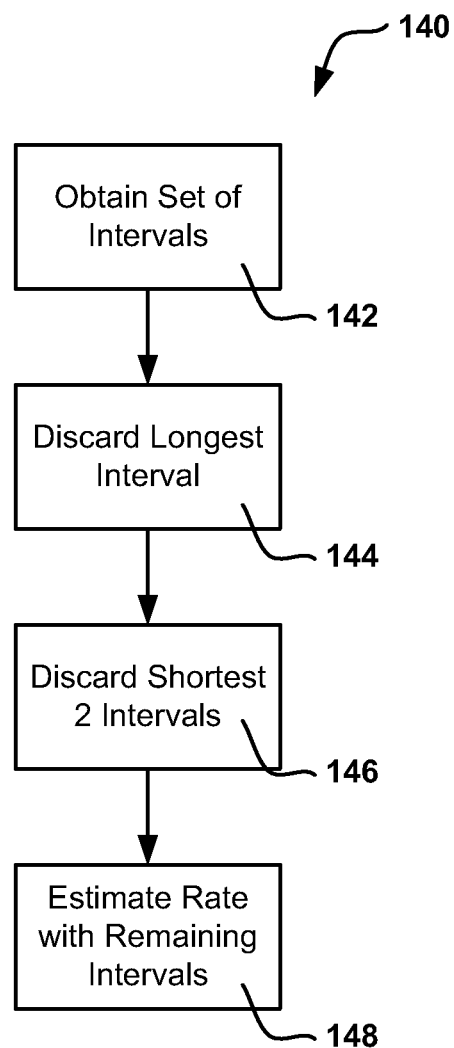
FIG. 7 shows a method of estimating cardiac rate by excluding selected intervals.

FIG. 7 shows an illustrative example in which selected intervals in a set of intervals are excluded from rate calculation. The method is shown at 140, and begins with a step of obtaining a set of intervals 142. The longest interval from the set is discarded from the current iteration of rate estimation at 144, and the shortest two intervals are discarded from the current iteration of rate estimation at 146. The remaining intervals which have not been discarded are then used to estimate the rate for the current iteration, as noted at 148. Step 144 can be omitted, if desired, or, in another embodiment, more than one longest interval is discarded. Step 146 can be modified to exclude more than two shortest intervals, if desired, or only one interval may be discarded.

For example, eight intervals may be obtained at set 142, with three excluded as shown in FIG. 7, leaving five intervals. A method that excludes the two shortest intervals and the one longest interval from a set of eight intervals and calculates an average of the remaining five intervals is referred to herein as a 5/8 Interval Method. Numerous alternative formulations can be used, such as:

6/8 (middle)—excluding the shortest and longest intervals from a set of 8

6/8 (long)—excluding the two shortest intervals from a set of 8

4/7 (offset)—excluding the two shortest and one longest interval from a set of 7

8/12 (middle)—excluding the two longest and two shortest intervals from a set of 12

5/6 (short)—excluding the longest interval from a set of six

In these examples, larger set sizes will smooth rate calculations but can delay identification of sudden-onset tachyarrhythmia. Several of the following examples will use the 5/8 Interval Method, but it should be understood that this choice is made for illustration and the invention is not limited to the 5/8 Interval Method unless specifically recited in the appended claims.

Returning to the earlier example of four overdetections in twelve R-waves, the noted interval sequence was:

{L, L, L, S, S, L, L, L, S, S, L, L, L, S, S, L, L, S, S,
L, L, L, L}

Where L indicates an accurately calculated interval and S indicates a shortened interval, where two consecutive "S" intervals equal the length of one L interval. Using the 5/8 Interval Method, the interval averages come out as:

{N, A, F, F, A, N, A, F F, A, A, F, F, F, A, N}

The resulting sixteen interval averages include seven fast (F) calculations having two short intervals among five included in the averaging, with three normal (N) calculations and six above actual (A) rate calculations having one short interval among the five. Thus, seven of sixteen (44%) calculations are fast (F) instead of thirteen of twenty (65%) with the direct four interval average—eliminating about a third of the fast (F) calculations.

Reducing, even if not eliminating, the quantity of fast (F) calculations can help avoid tachyarrhythmia declaration in a system using an X/Y counter. An "X/Y counter," as that term is used herein, uses Y as the size of the set of analytical conclusions under consideration, and X as the number of the Y analytical conclusions that indicate tachyarrhythmia. To declare tachyarrhythmia, systems using an X/Y counter are usually set so that X must constitute a majority or supermajority of Y, for example, in the range of 60-80% (12/16 or 18/24 may be used, for example).

In the above example having four overdetections in twelve R-waves, cutting the number of fast (F) calculations by a third reduces the chance that the X/Y counter stays close to or reaches the supermajority needed to declare tachyarrhythmia. Those skilled in the art recognize that once tachyarrhythmia is declared, the implantable system usually begins preparing for therapy (in the case of defibrillation) or may begin applying therapy (for antitachycardia pacing). If overdetection, rather than treatable arrhythmia causes therapy delivery or preparations for therapy, the device wastes energy and reduces its battery life and, if inappropriate therapy is delivered, may cause harm to the patient.

Several prophetic numeric examples follow. These examples are not based on actual working examples. These examples are provided to illustrate and compare rate calculation with a Four Interval Average to rate calculation with a 5/8 Interval Method.

Figure 8:
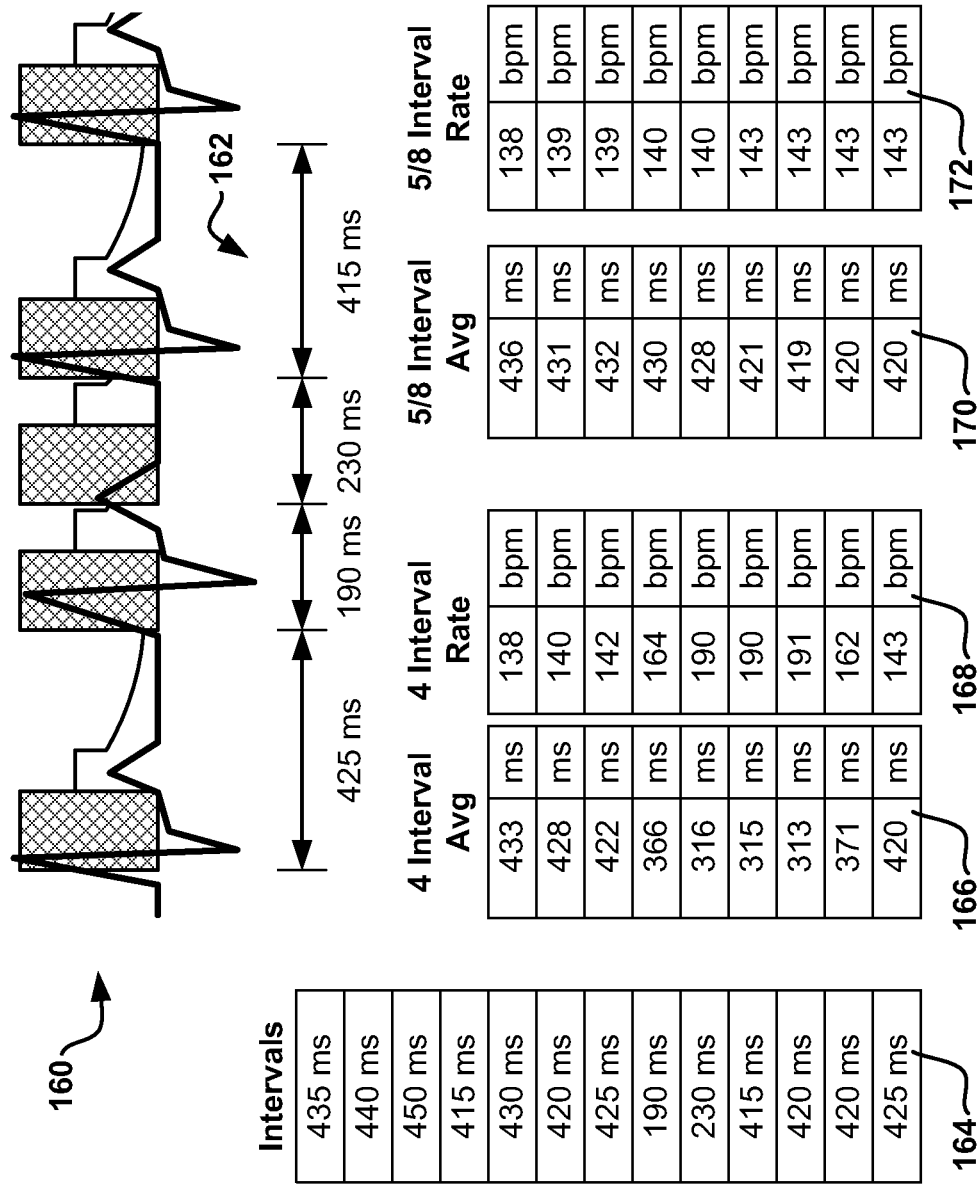
FIG. 8 compares methods of estimating cardiac rate in the presence of overdetection.

FIG. 8 shows an electrical signal represented at 160, with intervals shown at 162 and interval data at 164 corresponding to the intervals 162. Overdetection of the second cardiac cycle of the electrical signal 160 is shown, such that the intervals shown at 162 are 425 ms, 190 ms, 230 ms and 415 ms. The handling of this overdetection by two different methods is shown in the lower half of FIG. 8.

A larger block of intervals is shown at 164, with the four interval averages from this block of intervals 164 shown at 166. The rate as calculated using the four interval averages 166 is then shown at 168. For a 5/8 Interval Method, the calculated average intervals are shown at 170, and the resulting rates are shown at 172. As can be seen, the Four Interval Average approach allows the calculated rate to reach 190 bpm, which the 5/8 Interval Method avoids.

Figure 9:
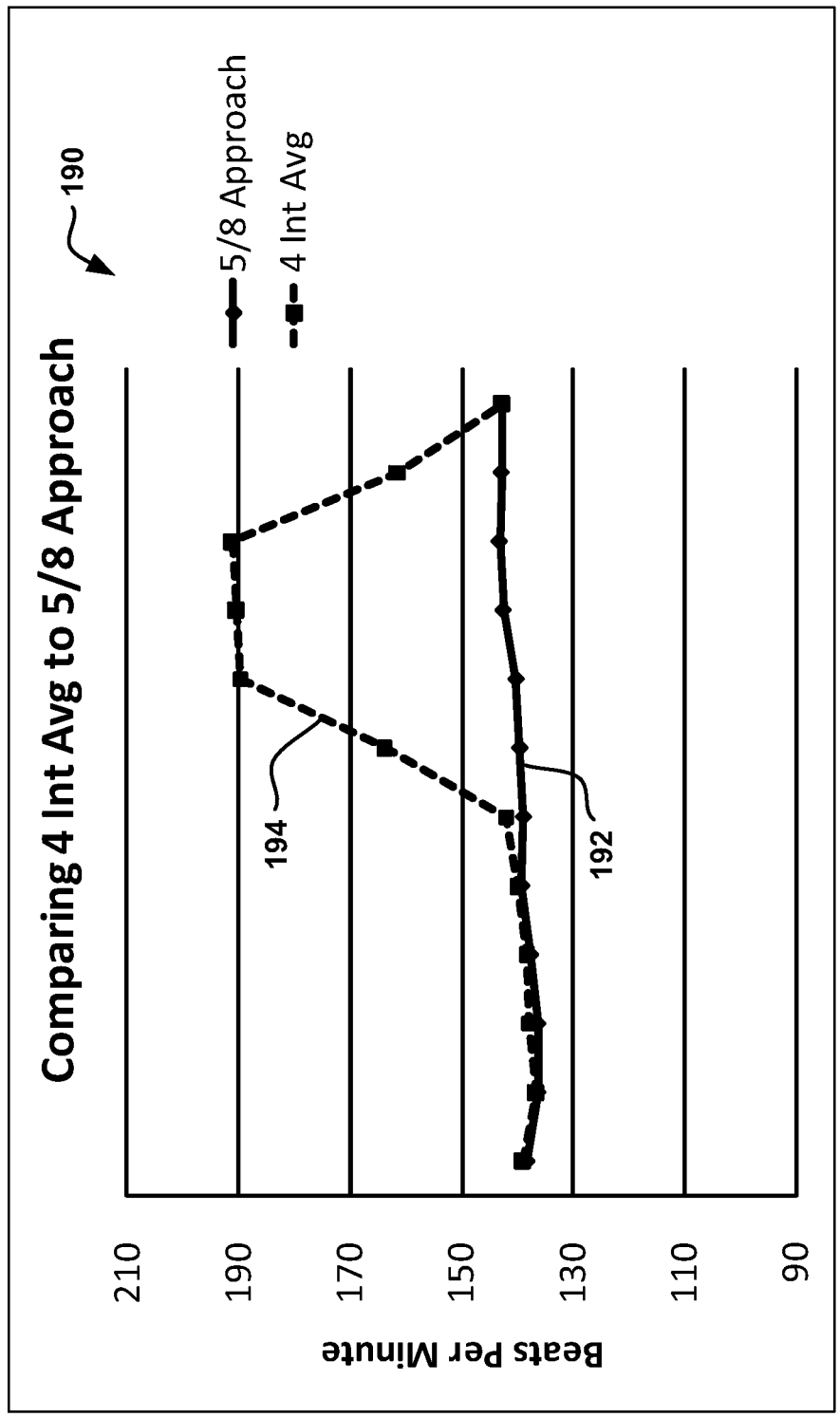
FIG. 9 graphs the comparison in FIG. 8.

FIG. 9 provides a visual representation of the data from FIG. 8. The graph 190 compares the cardiac rate as calculated using a 5/8 Interval Method (solid line 192) with the cardiac rate as calculated using a Four Interval Average. The rate as calculated using a 4-Interval Average 194 spikes upward due to the overdetection of a T-wave, while the rate as calculated using a 5/8 Interval Method 192 does not spike at all due to the overdetection.

In some instances overdetection occurs asymmetrically between two R-waves. The result will be two shortened intervals, a very short one (if T-waves are overdetected, likely the R-T interval) followed by a longer but still incorrectly shortened interval (often the T-R interval). If this is the case, a 5/8 Interval Method will discard the very shortest interval (the R-T interval) first. If multiple overdetections appear close-in-time to one another, the 5/8 rule will be able to discard the very shortest intervals repeatedly, while keeping normal intervals and also using the longest of the shortened intervals (T-R interval, in most cases). In some sensing vectors the P-wave may be the cardiac signal component that causes overdetection, which may also be asymmetric as the R-P interval may be longer than the P-R interval. If a wide QRS complex causes overdetection, asymmetry is likely as well. The hypothetical numeric example of FIGS. 10-11 assumes asymmetry.

Figure 10:
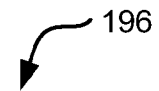
FIG. 10 compares methods of estimating cardiac rate in the presence of overdetection.

Referring to FIG. 10, a set of detection data is represented. The detection types are indicated in the leftmost column, where the "R" notations indicate detection caused by the R-wave, and the "T" notations indicate detection caused by the T-wave. The oldest detection is at the bottom. The interval duration is based on the interval between the detection occurring on the same line and the detection represented on the next line down.

In the next column to the right, intervals are classified by type depending on the detections that begin and end them. For illustrative purposes of this example, R-R intervals are assigned durations of 420 milliseconds (about 143 bpm), the R-T intervals durations of 180 milliseconds, and the T-R intervals durations of 240 milliseconds, as shown in the third column from the left. The use of R/T detection is merely illustrative; the analysis would also apply if R and P waves or P and T waves were overdetected or if wide QRS complexes were double detected.

In the middle column, the rate that would result from a Four Interval calculation is shown under the heading "4 Int. Rate," with resultant classifications shown under the "Classify" column third from the right. The "Classify" column is based on these rules:

1. Rates below 180 bpm classify as non-arrhythmic or "OK".
2. Rates above 230 bpm classify as indicating ventricular fibrillation, marked "VF."
3. Rates between 180 bpm and 230 bpm classify as ventricular tachycardia, marked "VT."

These particular descriptions are illustrative only, and other descriptions for the terms ("non-arrhythmic", "ventricular fibrillation", and "ventricular tachycardia") can apply. Continuing to the right on FIG. 10, the rate as calculated using a 5/8 Interval Method is shown under the heading "5/8 Rate." Finally, classification of the rates in the 5/8 Interval Method is shown in the last column on the right, again applying the above set of three rules.

A summary is provided in the box at 196. Using the Four Interval method to calculate rate, of the twenty-seven calculations noted, twenty-two were classified either VT or VF, with only five classified "OK". A ratio of 22/27 (81%) may lead the system to declare an arrhythmia episode. In contrast, the 5/8 Interval Method leads results in rate-based rhythm characterization of VT in only six of the twenty-three characterizations. A ratio of 6/23 (26%) would not lead most systems to declare an arrhythmia episode.

Figure 11:
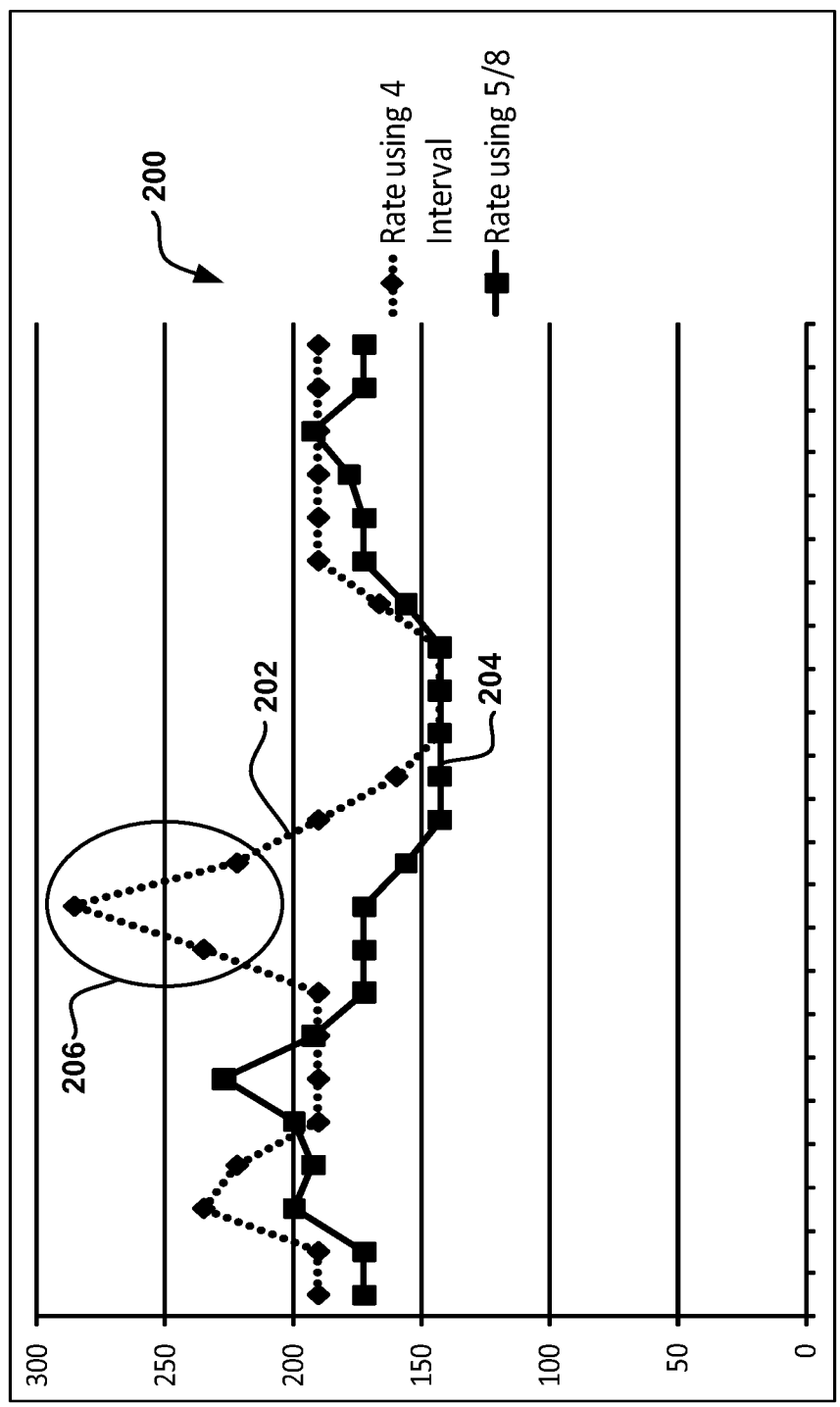
FIG. 11 graphs the comparison in FIG. 10.

FIG. 11 shows a graph of the rate calculations from FIG. 10. The cardiac rate as calculated using a Four Interval Average is shown in the dashed line at 202, and the cardiac rate as calculated using a 5/8 Interval Method is shown in the solid line at 204. As can be seen, the 5/8 Interval Method spikes once above a 200 bpm rate, but generally avoids the largest upward excursions of the Four Interval Method and is generally lower. For example, the Four Interval Average has three consecutive markers well over 200 bpm, as shown in the circle at 206. The 5/8 Interval Method avoids the spike 206 by exclusion of the shortest two intervals.

Another potential phenomenon is often referred to as "dropout." The sensed signal may drop in amplitude for a single cardiac cycle (or other period of time) for various reasons. When the sensed signal includes a cardiac cycle that goes undetected by the system, this can be termed "dropout." Dropout creates inappropriately long intervals relative to the actual cardiac cycle length. If the patient is in need of treatment (such as during ventricular fibrillation), dropout can delay therapy. This is because the long intervals caused by dropout may cause a system to incorrectly calculate a slow, non-tachyarrhythmic rate.

Figure 12:
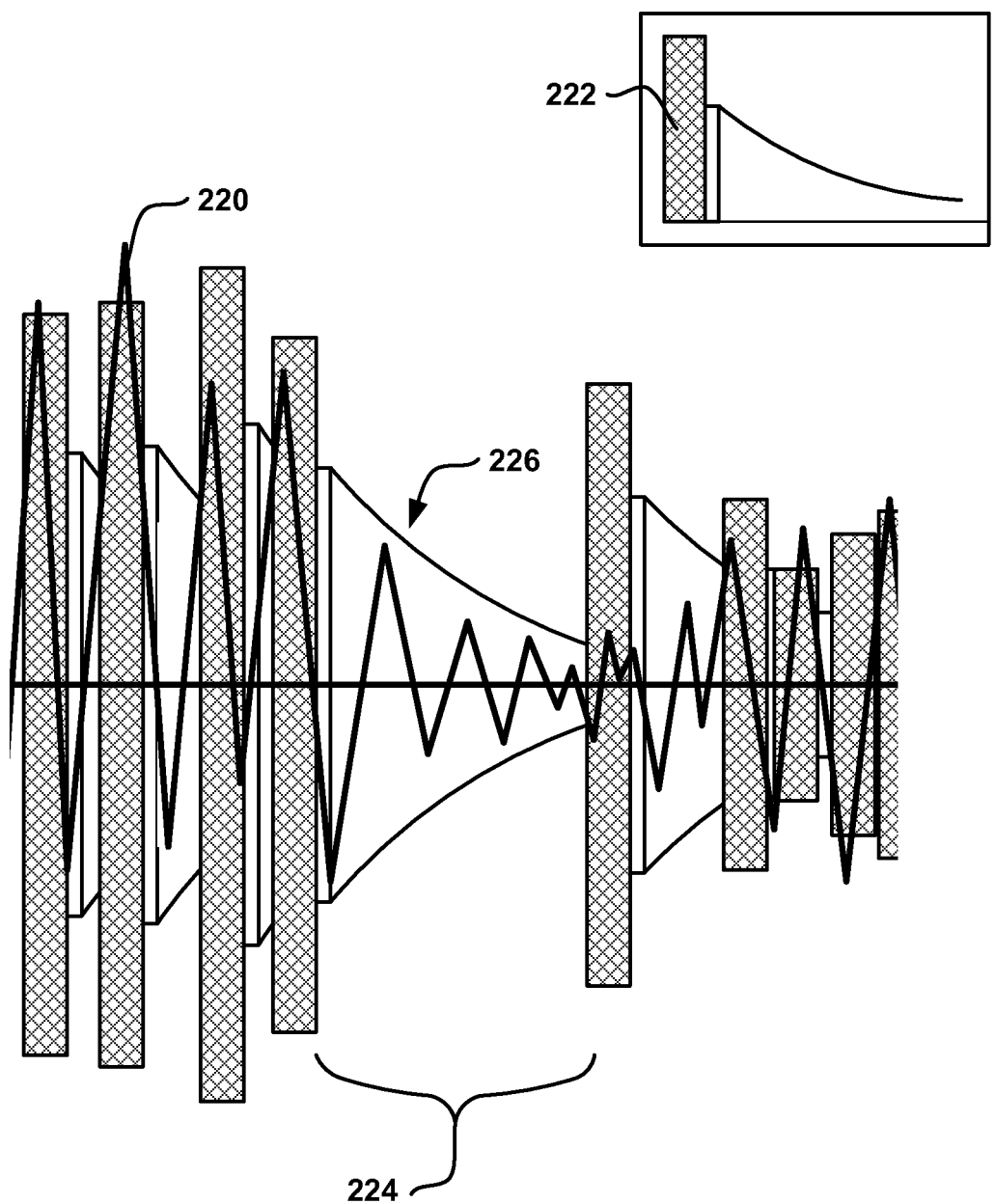
FIG. 12 graphically illustrates detection dropout during an arrhythmia.

FIG. 12 shows an example of dropout during a treatable arrhythmia. A cardiac signal is shown in the heavy line at 220 and displays features one would associate with a ventricular fibrillation. A detection profile as shown at 222 has been applied to the cardiac signal 220, resulting in numerous detections. Each shaded/cross-hatched box represents a refractory period associated with a new detection. As can be seen at 224, there is a long period of time in the middle of the Figure that does not include any new detections. This happens because the amplitude of the signal drops from several relatively higher amplitude detections on the left-hand side of FIG. 12 to much lower amplitude in the middle. As can be seen at 226, up to three peaks are missed. As the detection profile sensing threshold decays, it eventually chases the signal amplitude down to its lower level, but several detections are missed. The missed detections can be termed detection dropouts. The dropout can delay therapy by preventing detections that would fill an X/Y counter with indications of arrhythmia and by reducing the calculated event rate to a level that may fall below the applicable cut-off for tachyarrhythmia.

Figure 13:
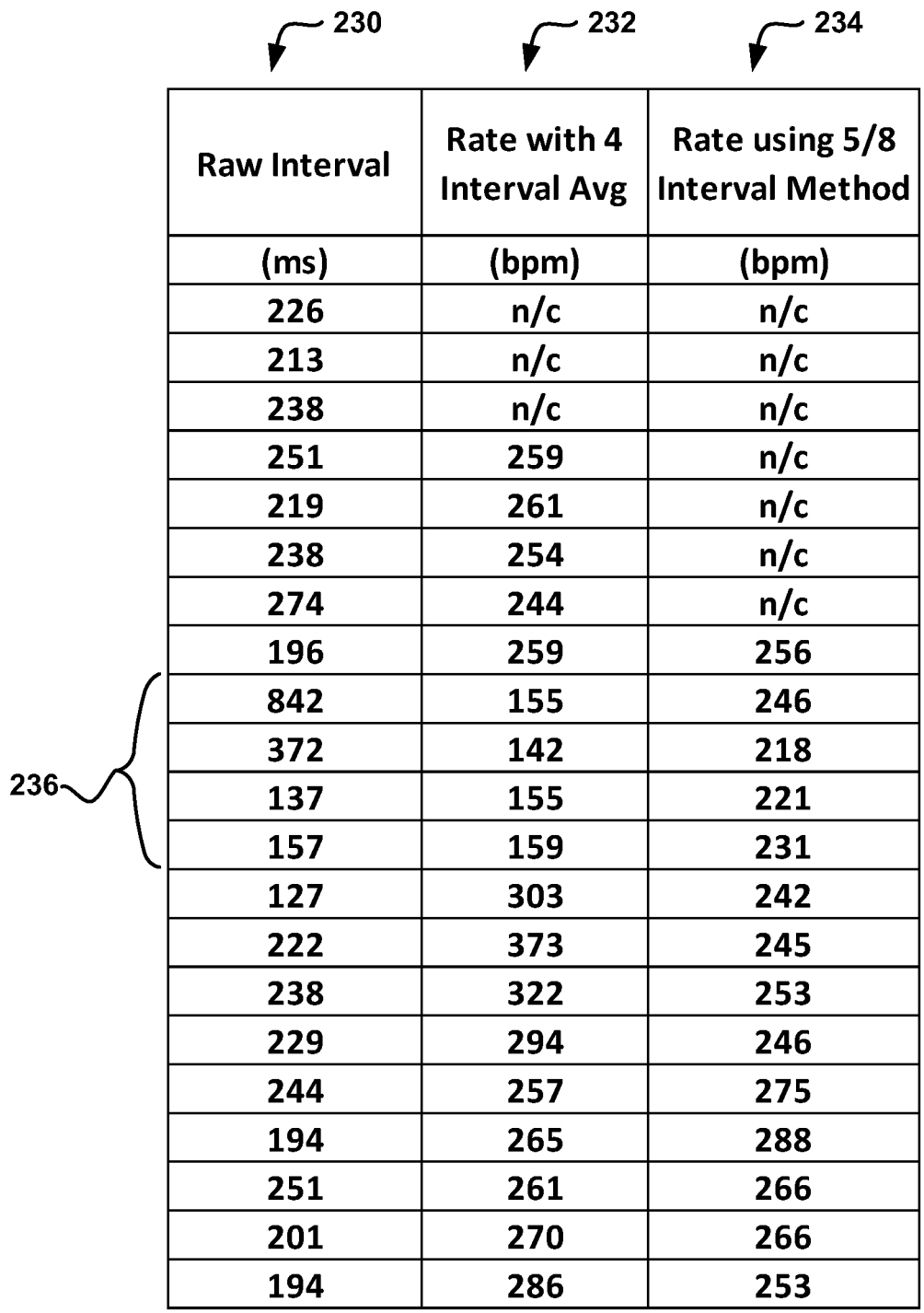
FIG. 13 compares methods of estimating cardiac rate in the presence of detection dropout, and FIG. 14 graphs the comparison in FIG. 13.

FIG. 13 provides a numeric example based on FIG. 12. The raw detected intervals 230 are shown in milliseconds, and rates in BPM as calculated using a Four Interval Average 232 and a 5/8 Interval Method 234 are displayed. The entries labeled n/c are not calculated as they would be based on intervals that are not shown in the table. As shown at 236, the dropout and its associated long intervals cause several iterations of the analysis using a Four Interval Average to find rates under one-hundred sixty bpm. This may result in a delay of therapy. For example, if an X/Y counter is being used, these four calculations at 236 could be considered non-treatable. For a relatively small counter (such as a 9-of-12 counter), four non-treatable analytical results would be enough to fail the X/Y counter until the data is cleared in a first-in, first-out manner.

In contrast to the rates as calculated with the Four Interval Average 232, the rates as calculated using a 5/8 Interval Method avoid the slow rates. Instead, rates calculated using the 5/8 Interval Method, as shown at 234, stay above two-hundred bpm throughout the numeric example. Thus, an X/Y counter (if used) would not be filled with incorrect, slow rate data that delays therapy. Statistically, the average rate over time remains approximately the same (about 250 bpm for each of columns 232, 234), but the variability is quite different (standard deviations are 62 bpm and 20 bpm for columns 232 and 234, respectively).

Figure 14:
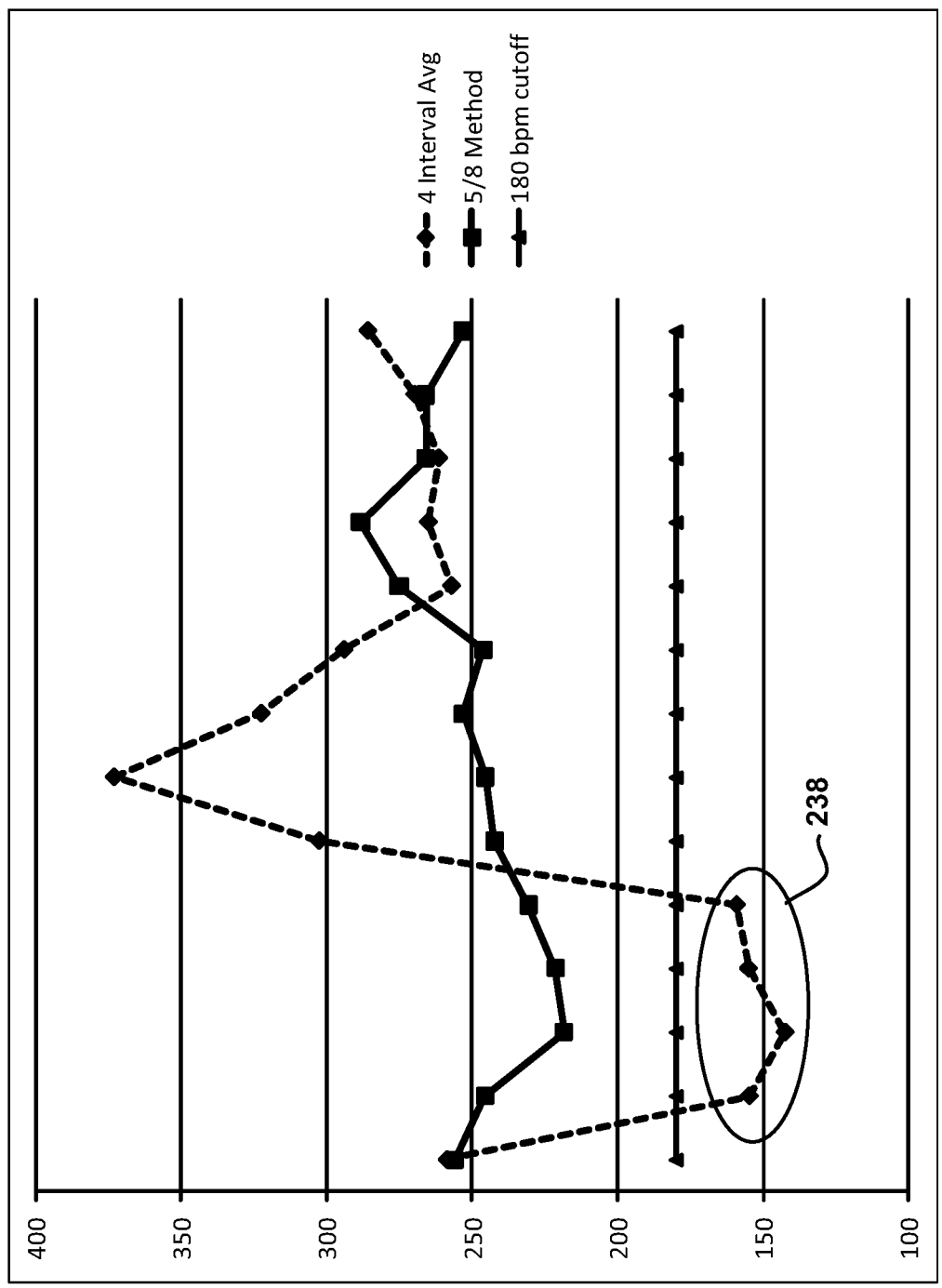

FIG. 14 graphs and compares two rate calculations from the numeric example of FIG. 13. In the illustration, 180 bpm is shown as a threshold for identifying tachyarrhythmia (the use of 180 bpm is merely illustrative). As can be seen at 238, dropout causes the rate calculation using a 4 Interval Average to cross below the 180 bpm threshold for several consecutive calculations, while the rate as calculated with a 5/8 Interval Method remains well above 200 bpm throughout. Dropout as shown in the 4 RR Avg calculation may delay therapy delivery and/or may divert therapy delivery, for example, causing antitachycardia pacing to be delivered first, rather than defibrillation therapy.

In some illustrative examples, rate estimation can take the same form at all times. For example, one illustrative embodiment applies a 5/8 Interval Method whenever the system is analyzing cardiac activity. In other examples, two rate calculation methods are used to conserve computation power by applying a fixed average calculation at low rates and a more complex method at higher rates. In one illustrative example, a Four Interval Average calculation is used at relatively low rates (below a rate cut-off) and a 5/8 Interval Method is applies at relatively higher rates.

Figure 15:
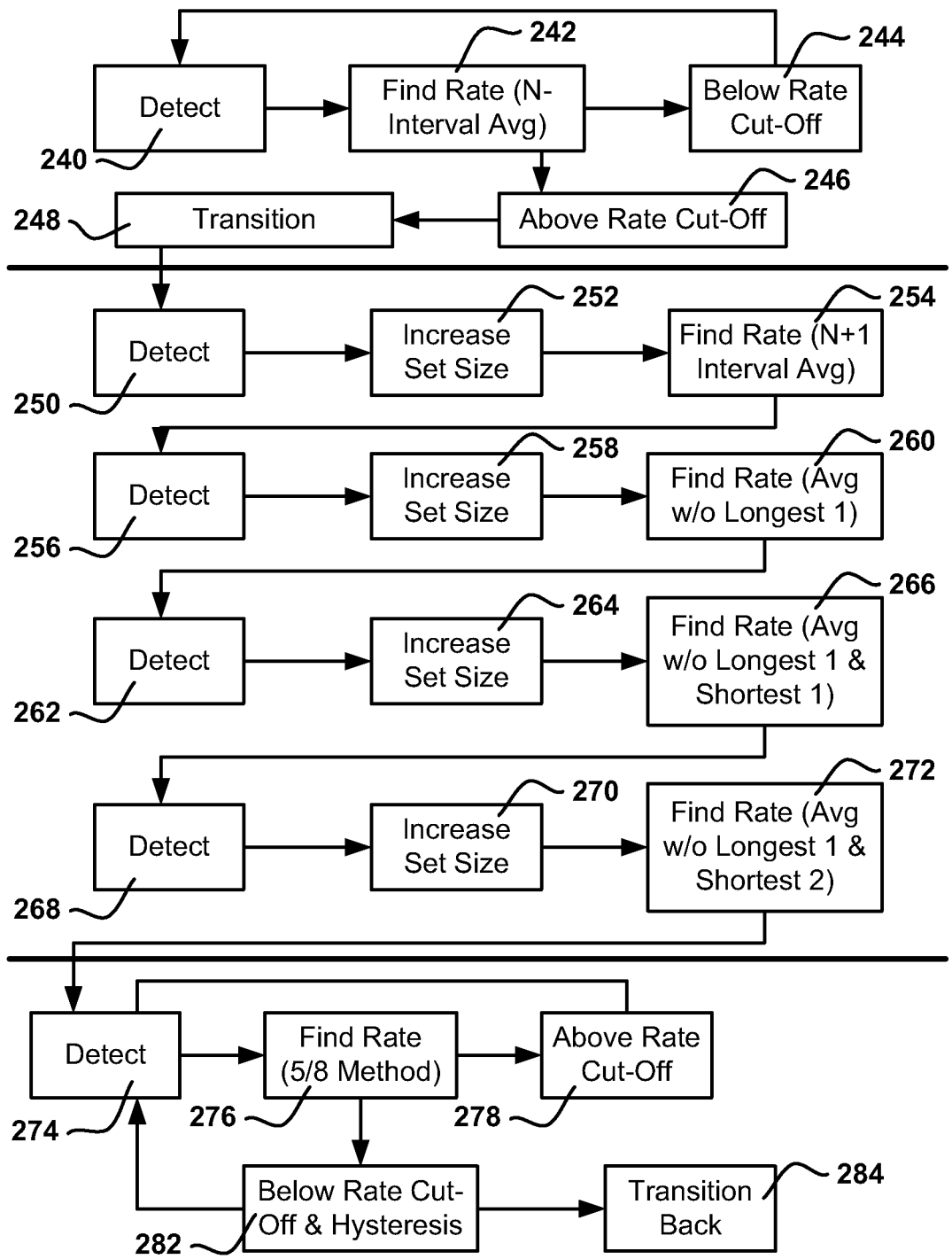
FIG. 15 shows an illustrative transition between methods for estimating cardiac rate.

FIG. 15 shows an example for transitioning from one rate estimation method to another. The example in FIG. 15 assumes the use of a Four Interval Average for low rates, and a 5/8 Method for higher rates, however, those skilled in the art will understand that other set sizes and configurations for excluding short or long intervals can be used instead. The method begins with detection of events 240. Next, the rate is found 242, using an N-Interval Average. The method next checks whether the rate is below or above a predefined Rate Cut-Off. For example, the Rate Cut-Off may be in the range of 140 bpm, or higher or lower, depending upon system design and preferences. If the rate is below the Rate Cut-Off 244, the method iterates back to detection 240.

If the rate is above the Rate Cut-Off 246, the method continues to a transition 248. Various other steps may occur during transition 248 (such as checking of signal quality or system errors, or activation of signal recording/memory functions), but the focus in FIG. 15 is on steps to transition from an N-Interval Average to a 5/8 Interval Method. The presumption in FIG. 15 is that the N-Interval Average is a Four Interval Average, and will transition to a 5/8 Interval Method.

Detection occurs at step 250, followed by increasing the set size 252 and finding rate 254. In this sequence 252-254, the method transitions from a Four Interval Average calculation to a Five Interval Average calculation by keeping all four intervals used previously and adding a fifth interval. Next, another detection occurs at 256, with additional increase in the set size 258 and calculation of rate 260 using a 5/6 Interval Method in which a set of six intervals (the five from 252/254 plus a new interval) is analyzed and the longest interval is discarded from the rate estimation, with the remaining five averaged to calculate an estimated rate. In another illustrative example, the shortest interval may be discarded from the rate estimation at 260, rather than the longest interval, with the longest interval(s) discarded in later iterations of the method at 266 and 272, below.

Following step 260, another sequence of detection 262, increase of set size 264 and rate estimation 266 occurs. This time the set is increased to seven intervals at block 264 (the six from blocks 258/260 plus one new interval). Now, a 5/7 Interval Method is used, with the longest and shortest intervals in the set of seven discarded and rate estimated using the remaining five.

Following step 266, another sequence of detection 268, increase of set size 270 and rate estimation 272 occurs. In this last explanation of the set size (at least in the method of FIG. 15), the set is increased to eight intervals at block 270 (the seven from blocks 264/266 plus one new interval). Finally a Five of Eight method is used in block 272 to estimate rate, with the one longest and two shortest intervals excluded.

The method then exits the transition to block 274. At block 274, detection is performed. Rate estimation using the 5/8 Interval Method 276 follows. The rate is then analyzed relative to a Rate Cut-Off threshold (which may be the same as or different from the Rate Cut-Off at blocks 244/246). If the rate is above the Rate Cut-Off 278, then the method continues in a loop at 274, 276, 278, during which various additional analyses and processes may occur as well, such as therapy decisions, preparations, annunciation, episode storage, etc. If the rate drops below the Rate Cut-Off 282, then the method may check for hysteresis rules and determine whether to transition back 284 to the N-Interval Average analysis loop 240, 242,244 or to simply return to detection 274. Example hysteresis rules may include requiring a selected number of iterations or passage of time using the 5/8 Interval Method before allowing a transition back to the N-Interval Averaging method, and/or applying a different Rate Cut-Off (for example a lower rate cut-off can be set at 278/282 than was used at 244/246).

In some examples, rate can be used to exit or terminate the transition 248 if the rate of detections drops back below the Rate Cutoff applied at 244/246. The reverse transition may also be terminated if the rate of detections rises above the Rate Cutoff applied at 278/282. In other examples, the method generally follows through regardless of rates found at blocks 254, 260, 266, 272. For example, the transition at 248 may rely on a rate cutoff of 150 bpm, with a single calculation being sufficient to trigger transition 248, while the transition at 284 may rely on a rate cutoff of 120 bpm and require ten consecutive calculations meeting the cutoff threshold before transitioning back.

Each of the detection steps 240, 250, 256, 262, 268 and 274 may incorporate an interval/event verification stage such as waveform appraisal (See U.S. Pat. No. 7,248,921, which is incorporated herein by reference, for example). In interval/event verification, the characteristics of an individual detected event are analyzed to determine it can be relied upon for rate estimation. An event showing indicia of noise (such as one or more of high frequency content, numerous peaks, saturation, or single-sided shape where all samples fall on one side of the baseline) may be considered unreliable and intervals around such an unreliable event may be discarded. For each of 250, 256, 262 and 268, "Detect" may include multiple event detection iterations until an interval between two not-unreliable detected events is found. If needed, a timeout may apply to any of these steps 250, 256, 262, 268 to escape the transition 248 in the presence of noise, directly transitioning to either detection loop 240-242-244 or detection loop 274-276-278.

The transition back from the 5/8 Method to the N-Interval Average may take several forms. In one example, as each new detected interval occurs, the two oldest intervals are removed from the maintained set, and the calculations at 266, 260 and 254 follow each iteration in an order reversed from that shown. Thus, from a 5/8 Interval Method, the transition may go to 5/7 without the longest and shortest intervals 266, then 5/6 without the longest interval 260, then to a Five Interval Calculation 254. In another example, the jump may go from 5/6 without the longest interval 260 directly to the Four Interval Average calculation. In another example, the reverse transition can be stopped if the newly calculated rate increases above the rate cut-off during transition. In yet another example, the transition can be an abrupt switch to the N-Interval calculation.

Figure 16:
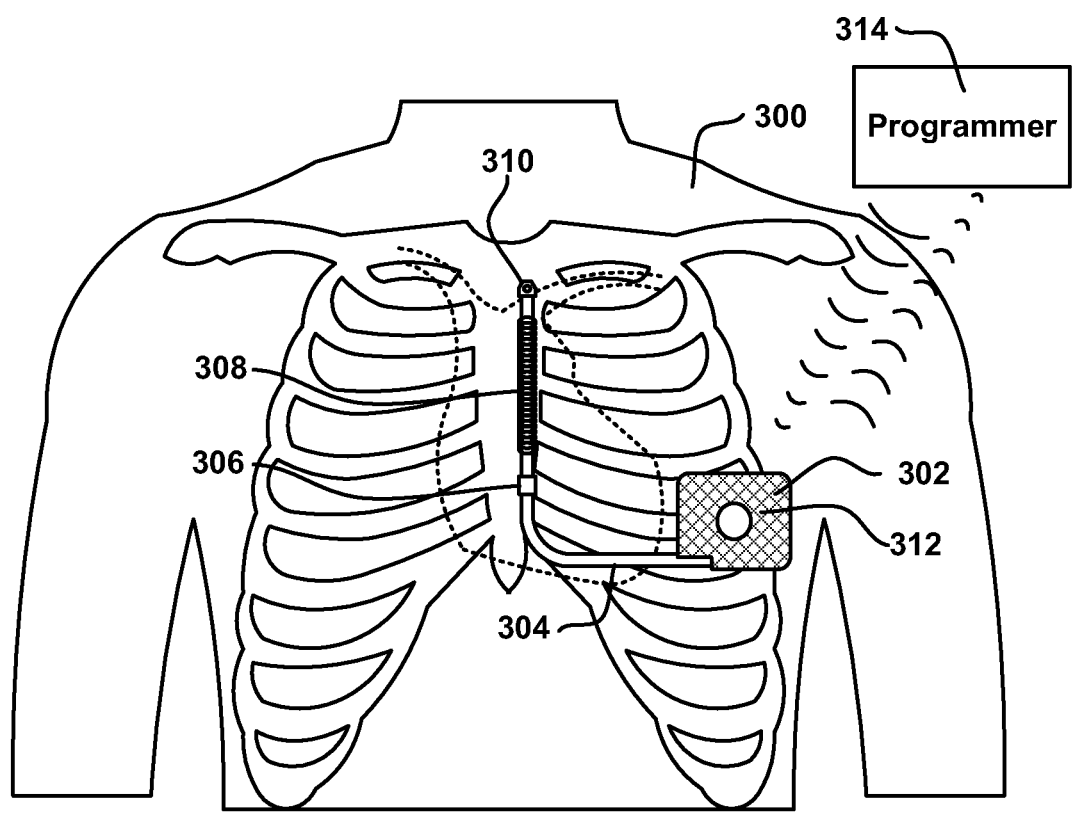
FIG. 16 illustrates an implantable cardiac stimulus system relative to a patient's anatomy.

FIG. 16 shows an illustrative implant location for one example. The illustrative implant location is a subcutaneous-only implant. The system is implanted in a patient 300, with a canister 302 placed near the left axilla at about the level of the inframammary crease. A lead 304 extends medially toward the xiphoid and then extends along the left side of the sternum toward the head of the patient 300. The lead 304 is shown with a plurality of electrodes 306, 308, 310, though more or fewer electrodes can be provided. Electrode 306, nearest the xiphoid, is shown as a ring electrode, middle electrode 308 is shown as a coil electrode, and tip electrode 310 is shown as a cap electrode having an attachment hole; these features and electrode designs may be interchanged, modified, or replaced with any suitable electrode design known in the art. Some illustrative designs are shown in US Patent Application Publication Numbers 20100152798 and 20120029335, and/or U.S. Provisional Patent Application Nos. 61/122,327 and 61/368,937, each of which is incorporated herein by reference. Additional examples which may also function are shown in numerous other patents and patent applications and/or are or once were commercially available as implantable electrodes of various types.

The canister 302 may include an electrode 312, which can be a discrete electrode, a portion of the surface of the canister 302, or may be the entire surface of the canister 302. The canister 302 preferably contains operational circuitry for the system. The operational circuitry may include a controller and any suitable analog and/or digital circuits needed for signal processing, memory storage and generation of high-power, low-power electrical or non-electrical outputs. The operational circuitry may be coupled to suitable battery technology for an implantable device, with any of numerous examples well known in the art, and may use various capacitor technologies to assist in the short term build-up and/or storage of energy for defibrillation or other high output purposes. The lead 304 and external shell for the canister 302 can be manufactured with various materials suitable for implantation, such as those widely known, along with coatings for such materials, throughout the art. For example, the canister can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes 306, 308, 310 and/or 312 can be formed of suitable materials as well, such as silver, gold, titanium or stainless steel such as MP35N stainless steel alloy, or other materials.

The location of system implant may vary. For example, the system shown is a subcutaneous-only system located on the anterior and lateral chest between the skin and ribcage of the patient. Other subcutaneous only systems (including systems without a lead 304 or with multiple leads 304) may be used with other anterior only placements and/or anterior-posterior, posterior only, left-right, etc. locations, including, for example, locations noted in U.S. Pat. Nos. 6,647,292, 6,721, 597, 7,149,575, 7,194,302, each of which is incorporated herein by reference, and other locations as well. Subcutaneous placement can include any location between the skin and ribcage, including sub-muscular. Further, rather than a subcutaneous-only system, a transvenous, epicardial or intravascular configuration may be used instead, and features of each type of system may be combined in any suitable manner.

A programmer 314 is shown as well. The programmer 314 and implantable system are preferably designed to communicate with one another during programming sessions. Such communication may include interrogation of device history and/or status, reprogramming of device settings, updating or downloading of new software/firmware, control of testing of the system such as induction or pacing testing, lead impedance or battery measurement, etc. While a programmer 314 is shown, it is understood that any suitable monitoring system (such as a home monitoring system) can take the place of the programmer 314 for any of these noted functions, as desired.

Several illustrative examples take the form of implantable cardiac stimulus devices such as implantable cardioverter-defibrillators, implantable pacemakers, and/or hybrid/combinations that include each of implantable defibrillator capabilities and implantable pacemaker capabilities. Other illustrative examples may include implantable cardiac monitors, which can use rate calculation methods to determine when and how to perform such functions as generating patient alerts, identifying captured signal data for storage, or any other suitable functions. Some examples of implantable monitoring or electrical therapy delivery systems may also include the ability to deliver pharmaceuticals, or any other suitable therapy.

Figure 17:
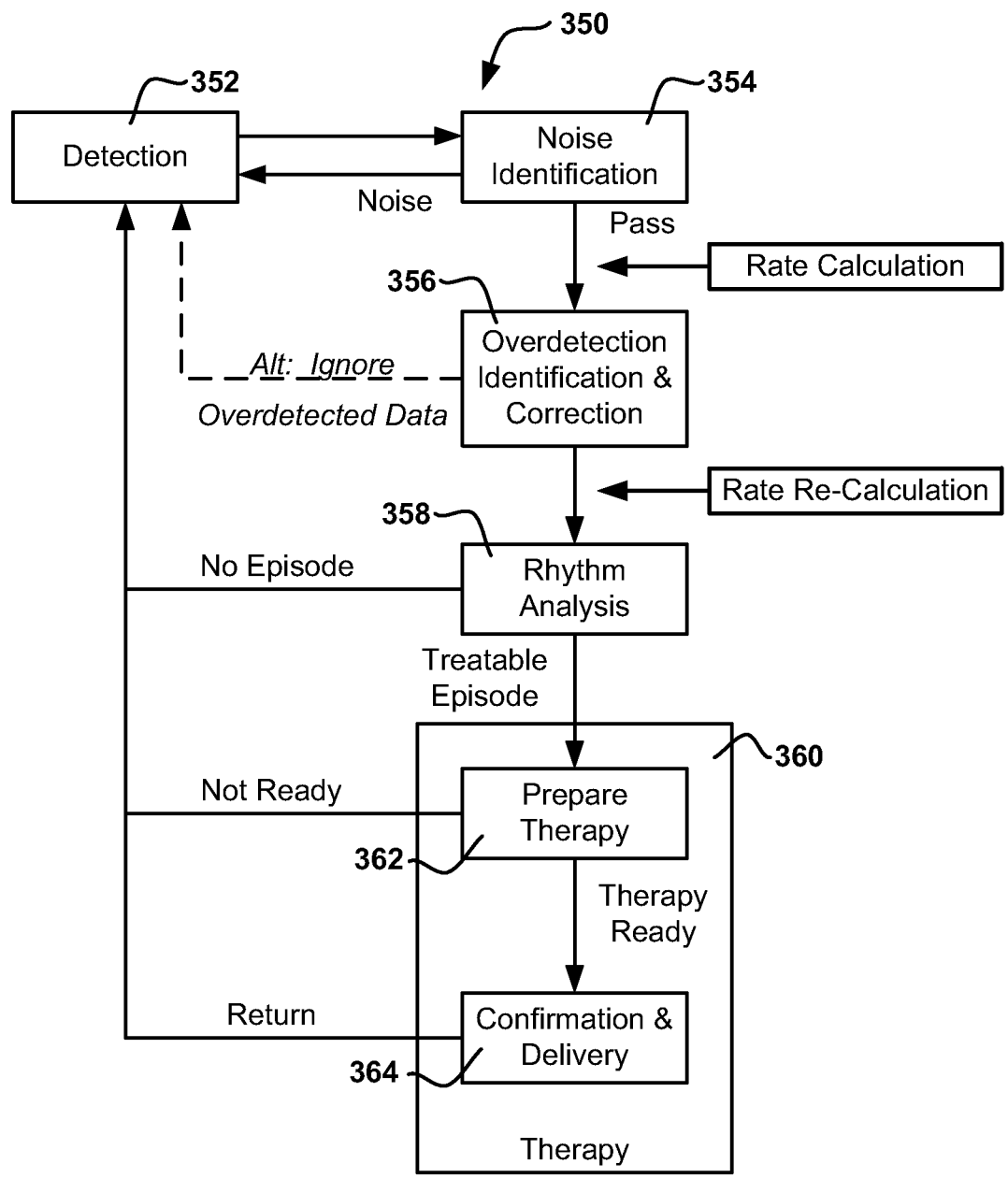
FIG. 17 shows a method of cardiac signal analysis including therapy delivery.

FIG. 17 provides a block flow diagram illustrating an example of a signal analysis for an implantable system. The method 350 is shown, for this example, as being detection driven with detection block 352 leading to a noise identification block 354. If noise is identified, the method returns to detection 352 to wait for a next new detection. If noise identification 354 is passed, the method continues to overdetection identification and correction, as shown at 356. If overdetection is identified at 356, associated data may be corrected to mitigate the impact of overdetection and, optionally, the method may return to detection 352. As indicated in FIG. 17, rate calculation can precede overdetection identification (which could optionally be bypassed if the rate calculation is sufficiently low) and rate may be re-calculated following overdetection identification at 356, either due to changes based on identification of overdetection(s) or if rate has not been calculated before overdetection identification 356 takes place.

Next is rhythm analysis 358, which can include analysis of the overall rhythm of the patient to determine whether therapy is needed. If therapy is not needed at block 358, the method returns to detection 352. Otherwise, the method may continue to block 360 for preparing and delivering therapy. In block 360, the system prepares therapy 362 for delivery, if needed. Preparing therapy 362 may include charging a capacitor to a therapy energy or other steps as desired. If therapy is not yet ready, the method returns to detection 352 to await another iteration. Once therapy is ready, the system may confirm the ongoing need for therapy and deliver therapy 364. If therapy confirmation fails, the system again returns to detection 352 to await another iteration. If therapy is ready and confirmation passes, then therapy is delivered and any needed post-therapy activity is undertaken.

Various additional details for, further features of, or alternatives to the system of FIG. 16 and/or the method in FIG. 17 can be found in the disclosures of the following patents and patent applications, which are incorporated herein by reference as showing further illustrative examples of implantable medical device systems/components, methods of their use, and accessories: U.S. Pat. Nos. 6,647,292, 6,721,597, 6,754,528, 6,865,417, 6,937,907, 6,952,608, 6,954,670, 7,065,407, 7,120,495, 7,149,575, 7,194,302, 7,248,921, 7,330,757, 7,359,754, 7,376,458, 7,392,085, 7,477,935, 7,555,338, 7,623,909, 7,623,913, 7,623,916, 7,655,014, and 7,769,457; US Pub. Pat. Apps. 20090036943 (now U.S. Pat. No. 7,962,212), 20090054796 (now U.S. Pat. No. 8,079,959), 20090187227, 20090198296 (now U.S. Pat. No. 8,244,349), 20090228057, 20090259271 (now U.S. Pat. No. 8,160,686), 20100004713 (now U.S. Pat. No. 8,160,687), 20100152798, 20100152799, and 20100331904, U.S. patent application Ser. Nos. 12/913,642 (now U.S. Pat. No. 8,265,737) and 12/913,647 (published as US Pub. Pat. App. 20110098775), and U.S. Prov. Pat. Apps. 61/368,937 and 61/375,732. The present invention is not limited to any of the particular examples shown in these commonly assigned patents or applications, and numerous alternatives will be recognized by those skilled in the art.

The above examples primarily use averaging of several intervals to establish a measure for rate. By dividing the average interval into sixty seconds, a measure of cardiac rate is obtained. In some examples, rather than averaging the remaining intervals, various mathematical measures can be taken. For example, a mean interval and error measure (such as standard deviation or variance) can be calculated, with the error measure integrated into subsequent analysis such that large error measures make a finding of arrhythmia more likely than small error measures. In one embodiment, the estimated rate is calculated conservatively by subtracting the error measure from the mean interval, which would elevate the calculated rate above that indicated by the mean or average interval by a factor related to the variability of the measured intervals. For example, a very low error measure (if the error measure is variance or standard deviation) may be indicative of a supraventricular arrhythmia which can be left untreated in many patients. In another example, the time series of intervals can be contemplated by providing different weight to each of the remaining intervals after exclusion of one or more longest and/or shortest intervals. For example, starting with eight intervals, if the two shortest and one longest interval are excluded, then the remaining five intervals can be integrated using a formula of the following type:

$$(m1)*(I1)+(m2)*(I2)+(m3)*(I3)+(m4)*(I4)+(m5)*(I5)$$
$$=\text{Estimated Interval}$$

Where m1, m2, m3, m4 and m5 are multipliers that add up to one, and I1, I2, I3, I4 and I5 are the remaining intervals from oldest to most recent. Illustrative multipliers would be:

$$m1=0.10\ m2=0.15\ m3=0.20\ m4=0.25\ m5=0.30$$

Such that the most recently captured intervals have the greater impact on the estimate of rate. Any other suitable computation may be integrated into the calculations as well.

Further embodiments adopt particular rules for the integration of various types of data in heart rate calculations. Some systems, for example, use additional methods of analysis to determine the reliability of detected events from sensed signals, such as those shown/discussed in U.S. Pat. No. 7,248,921, titled METHOD AND DEVICES FOR PERFORMING CARDIAC WAVEFORM APPRAISAL, which applies various criteria to identify detected events that are suspected of being non-cardiac in origin. Such "suspect" detected events can be marked as such, while other detected events can be marked as passing the appraisal of the waveform. Intervals between passing detected events may be considered waveform-appraisal passing intervals, while intervals that begin or end (or both) at suspect detected events are considered suspect events, in one example, while intervals that have not been parsed into these categories are considered raw intervals. Using this raw versus suspect/passing terminology, in some embodiments, the rate calculation can be performed on raw intervals, or it may be performed on only passing intervals.

Figure 18:
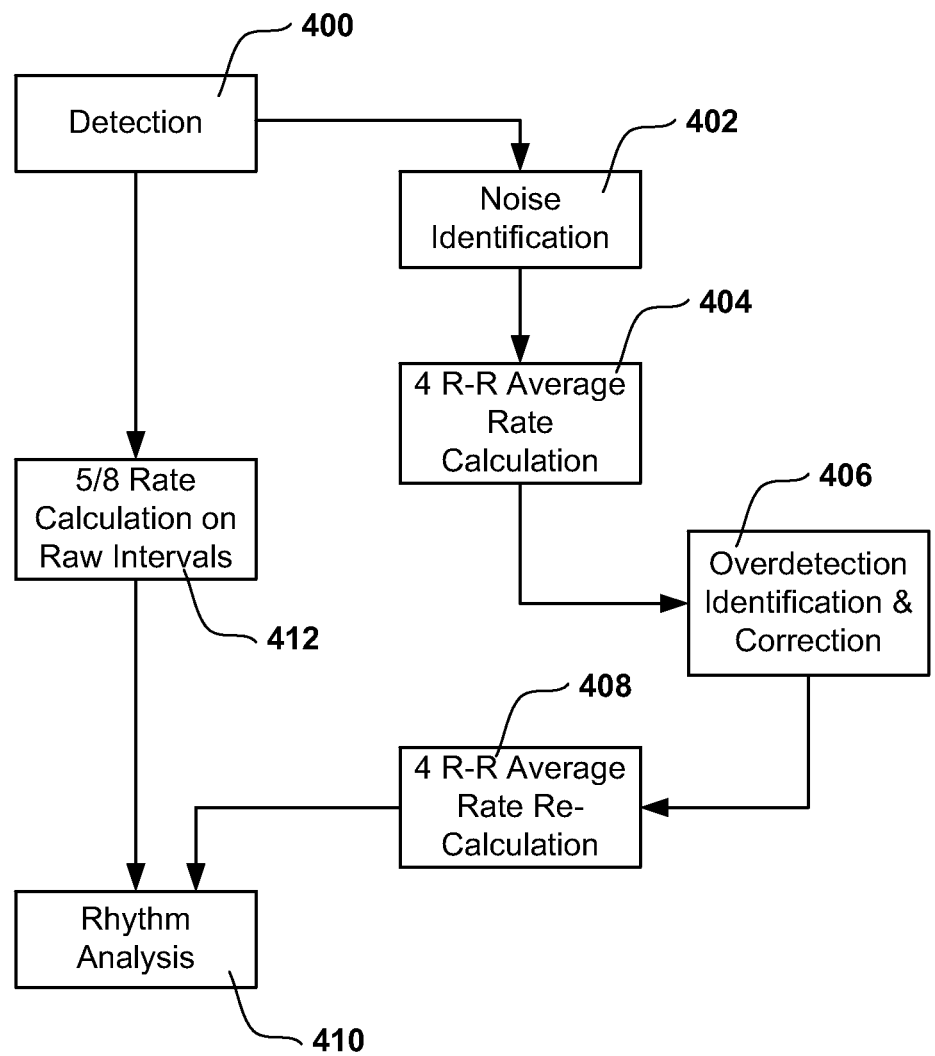
FIG. 18 illustrates a method of rate calculation using multiple paths.

An illustrative example of using raw intervals for rate calculation as well as noise-assessed and overdetection assessed intervals is shown in FIG. 18. In this example, two rate calculations can be performed side-by-side, with an N-interval average (such as 4-interval or 8-interval) performed using the noise-assessed and overdetection-assessed intervals, while an A out of B interval average (such as 5/8 Interval Method shown above) is performed on raw intervals. In the method illustrated by FIG. 18, detection 400 is performed as discussed above. Alone one path, the detected events/intervals are subject to noise identification at 402 and rate calculation using a four-interval average 404, followed by overdetection analysis 406 and rate recalculation 408, again using the four-interval average. In a separate path, the 5/8 rate calculation 410 is performed on the raw intervals from detection 400, without noise assessment 402 or overdetection assessment 406. The outcomes of these two calculations are received at rhythm analysis block 412. In one example, these outcomes are compared and the lesser of the two can then be selected for use in analysis. In another example, these outcomes are compared and, if largely different from one another, some further analysis (such as morphology analysis) may be called, or some action may be taken (such as switching sensing vectors or checking an additional sense vector).

In some embodiments, overdetection analysis methods are used to determine whether overdetection of the sensed signal is occurring, where more cardiac cycles are being counted/identified by the system than are likely actually occurring. In such examples, if overdetection is identified, rhythm classification can be suspended to avoid declaring a treatable arrhythmia in the presence of overdetection. In some examples, detection data may be corrected by identifying one or more detected events as overdetection and combining two (or more) intervals into a single longer interval spanning the identified overdetection. Where a combined interval is created, the system may prevent the combined interval from being eliminated from the interval average calculation as a "short" or "long" interval. If more combined intervals appear in the overall set than can be retained (for example, if using the 5/8 Interval Method, if there are 6 combined intervals in the set of 8), then the method may either use all of the combined intervals in calculating an average, or the method may eliminate non-combined intervals first and then proceed to eliminate whichever combined intervals are shortest or longest, depending on which slots for discarding shortest or longest intervals remain available.

In another illustrative embodiment, the identification of short and long intervals within the set of intervals can provide a basis for identifying overdetection. For example, if the two shortest intervals in the set are immediately next to one another, and the sum of the two shortest intervals equals the length of another intervals in the set within some reasonable boundary (+/−20 milliseconds, for example), then it may be likely that the two shortest intervals represent an overdetection between two accurate detections. The two shortest intervals may, in such circumstance, be combined into a single long interval. If desired, additional criteria may be applied by requiring the detected event that separates the two intervals must show a low correlation to a beat template, or by requiring that the detected event that precedes the earlier of the two short intervals demonstrate high morphology correlation to the detected event that follows the latter of the two short intervals, while the detected event separating the two short intervals fails to show high morphology correlation to the preceding and following detected events. Other additional criteria may apply as well, for example, comparing the width or amplitudes of the detected events surrounding the two shortest intervals. In another embodiment, none of these additional criteria are needed.

Any of the above discussed embodiments can be used to estimate heart rate. The heart rate, along with other factors, may be used in implantable cardiac stimulus systems (such as defibrillators, pacers and the like) to determine whether a malignant condition is likely occurring. Such systems can then deliver therapy, such as defibrillation, cardioversion or anti-tachycardia pacing.

In illustrative example, sensing means can be provided within the operational circuitry of an implantable device by providing typical and widely familiar combinations of filtering elements and amplifiers, as well as, if needed, switching circuitry, to allow signals from implantable (and implanted) electrodes to be retrieved and prepared for analysis. Detection means can be provided in discrete or microcontroller forms that allow for comparison of a signal from the sensing means to some detection thresholds, where such detection thresholds may take any form familiar to those skilled in the art of implantable cardiac devices. Set selection and generation means can take any suitable form, for example memory in or associated with a microcontroller or discrete storage systems, for track observed events or data. Rate calculation means may take any form of arithmetical analysis device such as a microcontroller or other logic, multiplier, divider or other circuitry. Where appropriate a microcontroller may be associated with memory for storing instruction sets (which may include separately called functions or numerous steps integrated into a larger whole) for performing activities such as event detection, set selection or generation, rate calculation or analysis, noise analysis, overdetection analysis, and/or rhythm analysis. Those skilled in the art will be readily familiar with the steps and methods needed to achieve implementation of such functionality within various hardware environments.

Those skilled in the art will recognize that the present invention may be manifested in a variety of forms other than the specific embodiments described and contemplated herein. Accordingly, departures in form and detail may be made without departing from the scope of the present invention.

What is claimed is:

1. A method of cardiac signal analysis in an implantable cardiac system for monitoring or treating a patient's heart, the implantable cardiac system including at least a plurality of implantable electrodes, the method comprising:
   sensing a signal using the implantable electrodes;
   detecting a series of events in the sensed signal, the series of events separated by intervals, to obtain a set of intervals;
   within the set of intervals, selecting a longest interval and generating a limited set of intervals that excludes the longest interval; and
   estimating a cardiac rate of the patient using the intervals in the limited set of intervals;
   wherein generating the limited set of intervals further comprises selecting the two shortest intervals within the set of intervals and excluding the two shortest intervals from the limited set of intervals.

2. The method of claim 1 wherein the limited set of intervals excludes the longest interval based only upon its status as longest among the set of intervals.

3. The method of claim 1 wherein the set of intervals includes 8 intervals, and the limited set of intervals includes 5 intervals, excluding the two shortest intervals from the 8 intervals and the longest interval from the set of 8 intervals.

4. The method of claim 1 wherein the set of intervals includes 7 intervals and the limited set of intervals includes 4 intervals and excludes the shortest two of the 7 intervals and the longest of the 7 intervals.

5. A method of cardiac signal analysis in an implantable cardiac system for monitoring or treating a patient's heart, the implantable cardiac system including at least a plurality of implantable electrodes, the method comprising:

sensing a signal using the implantable electrodes;

detecting events in the sensed signal, the detected events separated by intervals;

at a first time, using a first method to estimate a heart rate for the patient using information related to the detected events;

comparing the heart rate for the patient estimated using the first method to a rate threshold and determining that the threshold has been crossed;

at a second time after determining that the rate threshold has been crossed, using a second, different method to estimate the heart rate for the patient.

6. The method of claim 5 wherein:

the first method to estimate heart rate comprises averaging a set of intervals between detected events; and the second method to estimate heart rate comprises choosing intervals according to a set of interval selection rules and calculating a rate based upon the chosen intervals.

7. The method of claim 6 further comprising:

performing noise detection on the detected events and marking an interval before and an interval after a detected event that fails noise detection as suspect;

performing overdetection identification on any detected events that pass noise detection and combining an interval before and an interval after any detected events found to be overdetected into combined intervals and treating as discarded the two intervals used to form the combined interval;

wherein the interval selection rules comprise the following:

include any combined interval and exclude all suspect or discarded intervals;

exclude the shortest two intervals that are not combined intervals; and exclude the longest interval that is not a combined interval.

8. A method of cardiac signal analysis in an implantable cardiac system for monitoring or treating a patient's heart, the implantable cardiac system including at least a plurality of implantable electrodes, the method comprising:

sensing a signal using the implantable electrodes;

detecting a series of events in the sensed signal, the series of events separated by intervals, to obtain a set of intervals;

within the set of intervals, selecting a shortest interval and generating a limited set of intervals that excludes the shortest interval; and estimating a cardiac rate of the patient using the intervals in the limited set of intervals;

wherein the step of estimating a cardiac rate includes calculating a weighted average of the intervals in the limited set of intervals.

9. The method of claim 8 wherein the limited set of intervals excludes the shortest interval based only upon its status as shortest among the set of intervals.

10. The method of claim 8 wherein generating the limited set of intervals further comprises selecting a longest interval within the set of intervals and excluding the longest interval from the limited set of intervals.

11. The method of claim 8 wherein the limited set of intervals excludes the longest interval based only upon its status as longest among the set of intervals.

12. A method of cardiac signal analysis in an implantable cardiac system for monitoring or treating a patient's heart, the implantable cardiac system including at least a plurality of implantable electrodes, the method comprising:

sensing a signal using the implantable electrodes;

detecting a series of events in the sensed signals, the series of events separated by intervals, to obtain a set of intervals;

performing a noise detection analysis on the series of events to identify any suspect events and labeling an interval before and an interval after any suspect event as a suspect interval;

performing an overdetection analysis on the series of events to identify any overdetected events and combining an interval before and an interval after each overdetected event into a single combined interval;

performing a first rate calculation by taking a first subset of the set of intervals and reducing the first subset by excluding at least one shortest interval and at least one longest interval from the first subset to generate a reduced first subset and then calculating a first rate based on the reduced first subset;

performing a second rate calculation by taking a second subset consisting of a selected N intervals from the set of intervals where the N intervals are selected by excluding any suspect intervals and then taking N combined intervals and intervals that have not been combined from those that remain after excluding the suspect intervals, and calculating a second rate based on the second subset; and performing rhythm analysis using either the first rate or the second rate.

13. A method of cardiac signal analysis in an implantable cardiac system for monitoring or treating a patient's heart, the implantable cardiac system including at least a plurality of implantable electrodes, the method comprising:

sensing a signal using the implantable electrodes;

detecting a series of events in the sensed signals, the series of events separated by intervals, to obtain a set of intervals;

selecting a first set of intervals for a first rate calculation;

performing a first rate calculation by obtaining a mean and error measure for the first set of intervals and using the mean less the error measure to estimate cardiac rate for the patient.

14. The method of claim 13 wherein the error measure is selected from one of standard deviation and variance.

15. The method of claim 14 further comprising performing rhythm analysis by determining whether the error measure is less than a predetermined level and, if so, determining that the patient is not experiencing a malignant arrhythmia.

16. The method of claim 15 further comprising, if the error measure is not less than the predetermined level, analyzing one or more of rate and morphology of the cardiac signal to determine whether the patient is experiencing a malignant arrhythmia.

17. An implantable cardiac system for monitoring or treating a patient's heart, the implantable cardiac system including at least a plurality of implantable electrodes and a canister housing operational circuitry, the operational circuitry configured to perform a method of cardiac signal analysis:

sensing a signal using the implantable electrodes;

detecting a series of events in the sensed signal, the series of events separated by intervals, to obtain a set of intervals;

within the set of intervals, selecting a longest interval and generating a limited set of intervals that excludes the longest interval; and estimating a cardiac rate of the patient using the intervals in the limited set of intervals;

wherein the operational circuitry is further configured such that, within the method of cardiac signal analysis, generating the limited set of intervals further comprises selecting the two shortest intervals within the set of intervals and excluding the two shortest intervals from the limited set of intervals.

18. The implantable cardiac stimulus system of claim 17 wherein the operational circuitry is further configured such that, within the method of cardiac signal analysis, the limited set of intervals excludes the longest interval based only upon its status as longest among the set of intervals.

19. The implantable cardiac stimulus system of claim 17 wherein the operational circuitry is further configured such that, within the method of cardiac signal analysis, the set of intervals includes 8 intervals, and the limited set of intervals includes 5 intervals, excluding the two shortest intervals from the 8 intervals and the longest interval from the set of 8 intervals.

20. The implantable cardiac stimulus system of claim 17 wherein the operational circuitry is further configured such that, within the method of cardiac signal analysis, the set of intervals includes 7 intervals and the limited set of intervals includes 4 intervals and excludes the shortest two of the 7 intervals and the longest of the 7 intervals.

* * * * *